(12) United States Patent
Gorka

(10) Patent No.: US 9,649,402 B2
(45) Date of Patent: *May 16, 2017

(54) WOUND DRESSING

(71) Applicant: LOHMANN & RAUSCHER GMBH & CO. KG, Neuwied (DE)

(72) Inventor: Marius-Thomas Gorka, Mulheim-Karlich (DE)

(73) Assignee: LOHMANN & RAUSCHER GMBH & CO. KG, Schoenau (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,835

(22) Filed: Jul. 31, 2014

(65) Prior Publication Data

US 2014/0341969 A1 Nov. 20, 2014

Related U.S. Application Data

(63) Continuation of application No. 13/473,138, filed on May 16, 2012, now abandoned.

(30) Foreign Application Priority Data

May 19, 2011 (EP) .................................. 11004167

(51) Int. Cl.

| A61L 15/24 | (2006.01) |
|---|---|
| A61L 15/34 | (2006.01) |
| A61L 15/22 | (2006.01) |
| A61F 13/00 | (2006.01) |
| A61L 15/44 | (2006.01) |
| A61L 15/60 | (2006.01) |
| A61L 15/28 | (2006.01) |

(52) U.S. Cl.
CPC ........ *A61L 15/24* (2013.01); *A61F 13/00017* (2013.01); *A61L 15/225* (2013.01); *A61L 15/28* (2013.01); *A61L 15/34* (2013.01); *A61L 15/44* (2013.01); *A61L 15/60* (2013.01); *A61F 2013/00519* (2013.01)

(58) Field of Classification Search
None
See application file for complete search history.

(56) References Cited

U.S. PATENT DOCUMENTS

| 5,618,882 | A | 4/1997 | Hammond et al. | |
|---|---|---|---|---|
| 5,633,286 | A * | 5/1997 | Chen | 524/474 |
| 6,270,792 | B1 | 8/2001 | Guillemet et al. | |
| 6,369,289 | B1 | 4/2002 | Orr et al. | |
| 8,008,398 | B2 | 8/2011 | Muyldermans et al. | |
| 2005/0123590 | A1 | 6/2005 | Burton et al. | |
| 2005/0249791 | A1 | 11/2005 | Hobbs et al. | |
| 2007/0253911 | A1 | 11/2007 | Tamarkin et al. | |
| 2009/0155339 | A1 | 6/2009 | Eggerstedt et al. | |
| 2010/0092544 | A1 | 4/2010 | Okada et al. | |
| 2010/0179493 | A1 | 7/2010 | Heagle et al. | |
| 2010/0318052 | A1 | 12/2010 | Ha et al. | |
| 2011/0091551 | A1 * | 4/2011 | Baur et al. | 424/484 |
| 2012/0294927 | A1 | 11/2012 | Gorka | |

FOREIGN PATENT DOCUMENTS

| FR | 2783412 | 9/1990 |
|---|---|---|
| FR | 2916356 | 5/2007 |
| WO | WO 2007/000590 | 1/2007 |

OTHER PUBLICATIONS

European Search Report for European patent application 11 004 166.2 of Oct. 18, 2011 (English Translation).
European Search Report for the corresponding European patent application 11 004 167.0 of Oct. 18, 2011 (English Translation).
Jin Kon Kim, Dae Sung Jung, Jinhwan Kim; Morphology and rheological behavior of mixtures of poly (styrene-b-ethylene-co-butylene-styrene) block copolymer and poly (2,6-dimethyl-1-4, phenylene ether); Polymer, 1993 34:22, pp. 4613-4624.
Wadstrom, et al. "Hydrophobized wound dressing in the treatment of experimental *Staphylococcus aureus* infections in the young pig", Acta path. microbial. immunol. Scand. Sect B, 93, pp. 359-363 (1985).
Flosenzier, et al. "Polymer Engineering and Science" vol. 30 No. 1, pp. 49-58 (1990).
FOR and NOL can be found in U.S. Appl. No. 13/473,138.
Handbook of Pressure-Sensitive Adhesives and Products, edited by Istvan Benedek & Mikhail M. Feldstein, CRC Press, Taylor & Francis Group, 2009.

* cited by examiner

*Primary Examiner* — Nissa Westerberg
(74) *Attorney, Agent, or Firm* — Stinson Leonard Street LLP

(57) ABSTRACT

The invention relates to a sterile wound dressing having a backing and a nonabsorbent elastomer wound contact layer, wherein the elastomer matrix is formed by a synthetic three-block elastomer, preferably a copolymer of polystyrene block and polyolefin block (SEPS, SEBS, SEEPS, etc.) or mixtures thereof, wherein the total polymer content is less than 3.2 wt %, in particular 3.0 wt % or less, preferably 2.6 wt % or less, and is plasticized by an apolar oil and/or petroleum jelly.

14 Claims, No Drawings

WOUND DRESSING

CROSS-REFERENCE TO RELATED APPLICATIONS

This application claims priority to and is a continuation of U.S. patent application Ser. No. 13/473,138, filed on May 16, 2012, which claims priority to European Patent Application No. 11 004 167.0, filed on May 19, 2011, each of which is incorporated herein by reference in its entirety.

STATEMENT REGARDING FEDERALLY SPONSORED RESEARCH OR DEVELOPMENT

Not applicable.

BACKGROUND OF THE INVENTION

The invention relates to a sterile wound dressing with a backing and an elastomeric polymer matrix as the wound contact layer.

Wound dressings containing fat have been used successfully for many years for topical treatment of traumatic wounds such as cuts and scrapes and chronic wounds, such as decubital ulcers, leg ulcers, and the like, as well as burns on humans and animals.

LOMATUELL H from the company Lohmann & Rauscher GmbH & Co. KG ("L&R") is tulle impregnated with fat and is one of the products often used for medical care of skin wounds. This product, which is formed from a woven cotton impregnated with a fatty substance based on petroleum jelly, nevertheless has disadvantages such as loss of fatty substances to the handling tools (such as gloves) and to the wound and the wound environment. When it comes in contact with the wound, the petroleum jelly softens because of the increase in temperature and tends to be displaced to the periphery of the dressing.

This phenomenon often results in the backing being exposed and coming in direct contact with the wound. If the backing sticks to the wound, this often leads to traumatic changing of the dressing and a disturbance in the wound healing process.

Other commercially available products, e.g., the dressing from Johnson & Johnson ADAPTIC, which is a knit viscose material impregnated with an oil-in-water emulsion, or the product JELONET (Smith & Nephew), which is cotton gauze impregnated with paraffin, fulfill the same purpose as LOMATUELL H but also have properties that are a disadvantage with respect to the loss of fatty substances.

Furthermore, it seems that the known dressings of the fat-impregnated tulle type are too hydrophobic during use and facilitate an unwanted drying of the wound.

It is consistent with the general knowledge that the addition of a small amount of hydrophilic substances from the hydrocolloid group, such as carboxymethyl cellulose ("CMC") in dispersion to a hydrophobic elastomer matrix partially increases the hydrophobicity of the matrix after coming in contact with the wound exudate by forming a gel on the surface. This mixture of hydrophobic and hydrophilic properties of the surface of the matrix which comes in direct contact with the wound leads to a result that is extremely favorable for the wound healing process: an optimal degree of moisture maintained at the surface plus the presence of fatty substances which isolate the structure of the dressing and lead to faster wound healing, and a complete absence of adhesion of the compress to the wound.

A wound dressing having a liquid-permeable substrate, which is provided with openings and has an absorbent (at least 50% of the dry weight) non-adhesive polymer composition that contains a hydrophobic organic polymer matrix, a plasticizer and hydrophilic organic microparticles plus optionally bioactive agents is described in EP 1 691 851 B 1. The aforementioned document describes synthetic and natural bioactive agents. When these agents are used, it has proven problematical that the absorbent (superabsorber) in the dressing binds liquid in a gel form. The openings for exudate (e.g., viscous) become almost impassable due to this swelling process. Free removal of the exudate into the absorbent secondary dressing may then be hindered. Under some circumstances, this may cause maceration of the wound.

Sticking of the dressing to the wound can be prevented by using a sterile nonsticking compress according to EP 1 143 895 B 1. This compress contains a polymer composition of a thermoplastic elastomer, an oily plasticizer, petroleum jelly, and hydrophilic particles of a hydrocolloid (CMC, alginate, pectin) and optionally an active ingredient. According to a preferred embodiment of the invention described in this document, the elastomer matrix comprises a three-block elastomer, in which the concentration of the elastomer should be at least between 3.2% and 8.8%, so that the use of a cohesive, elastic polymer matrix which is stable in a moist medium can be ensured.

It is desirable to allow only very limited direct contact between the elastomeric polymer and the wound, such that this contact takes places essentially via the oily compounds, which are tolerated better by the living tissue of the wound than the elastomers are. On the other hand, the use of polymers is absolutely essential, with the total polymer content according to EP 1 143 895 amounting to at least 3.2% in order to ensure adequate cohesion and elasticity of the entire matrix.

EP 127 229 B1 describes an antiseptic compress which has a wound contact layer of an elastomer matrix, an apolar oil, a hydrocolloid (sodium carboxymethyl cellulose) as a dispersion and at least one surfactant (Tween 80), optionally with at least one antimicrobial agent (silver sulfadiazine). In a preferred embodiment of the invention described in the aforementioned document, a compress has a high total concentration of the synthetic three-block elastomer of more than 4.6 parts by weight. This is problematical in view of the desired avoidance of direct contact between the elastomer and the wound. Furthermore, the use of surfactants is not without problems because they have a certain cytotoxic potential.

EP 0 521 761 describes a nonsticking hydrophobic occlusive dressing consisting of a backing bonded to the matrix surface, wherein the elastomer matrix contains at least 10 30 parts by weight of a block copolymer and 70-90 parts by weight of a plasticizer, preferably petroleum jelly.

In order for all these wound dressings to be usable to promote healing without the risk of microbial contamination, they must first be sterilized. Wound infections have been shown to delay healing. They are caused by pathogenic microorganisms which penetrate into the wound (possibly through the wound dressing), replicate there, and produce toxins which act on the wound tissue itself as well as on the body as a whole.

There are various techniques for destroying contaminating microorganisms. In addition to sterilization by saturated steam or by dry heat, sterilization by gas (ethylene oxide, formaldehyde) or sterilization by irradiation are used routinely. However, none of these techniques is suitable without reservation for production of products, in particular those with pharmaceutical applications and in particular products which contain a fat-based elastomer matrix. Sterilization by saturated steam or dry heat therefore cannot be used because the elastomer matrix and the hydrocolloid do not tolerate high temperatures and extremely high atmospheric humidity well.

Likewise, sterilization by gas is generally avoided because of the inherent risk of the presence of residual gas in such wound dressings. Furthermore, with this technique it is not usually possible to obtain a distribution of the sterilizing agent over the entire volume of the elastomer polymer composition, which limits its efficacy.

In general, the use of a sterile barrier (primary packaging material), which preserves the sterility of the product during marketing until it is used on the patient, prevents the use of most of the aforementioned sterilization methods because an airtight packaging material has been selected to suppress the oxidizing influence of atmospheric oxygen as well as the influence of atmospheric oxygen on the hygroscopic hydrocolloid dispersed in the matrix.

Consequently, the technique generally used for sterilization of such wound dressings is sterilization by irradiation, which thus ensures very effective sterilization into the interior of the product. Two types of radiation may be used for this purpose, namely β- and γ-radiation.

The sterilization dose is adjusted within the context of a dose determination as a function of the initial microbiological burden (bioburden), i.e., the amount of microorganisms present in/on the product prior to sterilization.

To ensure effective decontamination with an adequate safety margin, an average dose of 25 kGray is generally used for the products to be sterilized. In practice, a product receives a dose between 25 and 40 kGray, depending on the method used.

However, these two known techniques of radiation sterilization also have unwanted effects on the treated elastomer matrix. In particular, the energy introduced into the matrix by this radiation is high enough to break the carbon-carbon bonds and carbon-hydrogen bonds in the elastomers used and to also cause breaks in the chains in these polymer macromolecules and thereby reduce their average molecular weight, which in turn influences/reduces their properties, in particular their cohesion ability.

Consequently, these aforementioned products are not completely satisfactory either because of difficulties associated with handling in applying or removing the dressing or because of a relatively high polymer price or a certain tissue intolerance of the elastomer polymers or due to the loss of cohesion after radiation sterilization.

BRIEF SUMMARY OF THE INVENTION

In view of the problems in the state of the art as described above, the object of the present invention is to make available an especially biocompatible nonsticking (optionally slightly adhesive) wound dressing based on an elastomer matrix containing fat and hydrocolloid with an improved resistance to radiation sterilization for treatment of traumatic and chronic wounds as well as burns.

According to the invention, this object is achieved by a refinement of the known wound dressings, characterized essentially in that the wound contact layer contains an elastomer matrix comprising less than 3.2% of an elastomer, in particular 3.0% or less, preferably less than 2.7% of a total polymer component, so that better tissue compatibility is obtained in addition to the economic advantage.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF THE INVENTION

In an especially preferred embodiment of the invention, thermoplastic elastomers ("TPE") and/or elastomer mixtures with an especially high molecular weight are used to counteract the negative effects of radiation sterilization on cohesion of the matrix. It has surprisingly been found that the addition/use of the preferred ultrahigh molecular elastomers such as Septon 4077 greatly improves cohesion after sterilization.

Due to the content of relatively temperature-sensitive components such as petroleum jelly or CMC in the matrix, the processing temperature is limited (preferably max. approximately 140-145° C.). The expected increase in the processing temperature when using an ultrahigh molecular elastomer is only minor, however, and is within the acceptable range.

The wound contact layer of a wound dressing according to the invention according to the invention preferably comprises, in addition to an organic polymer matrix, a plasticizer, and hydrophilic organic and/or inorganic microparticles which form a gel on contact with an aqueous solution.

According to one of the features of the invention, the wound dressing comprises a flexible open mesh fabric, wherein the fabric comprises fibers sheathed with an elastomeric cohesive and nonsticking gel/matrix, so that the mesh essentially cannot be clogged, i.e., remains permeable.

The polymer matrix may contain a synthetic thermoplastic hydrophobic three-block copolymer A-B-A, in which the polymer matrix preferably contains no more than 3.2 parts by weight, in particular no more than 2.6 parts by weight of a block polymer, in which the terminal block A may be of the polystyrene type and the central block B may be of the saturated polyolefin type and the styrene component is between 25% and 40%.

To obtain a hydrophobic matrix according to the invention with adequate cohesion even after radiation sterilization, three-block elastomers of the polystyrene-polyethylene-polybutylene-polystyrene (SEBS) type, or polystyrene-polyethylene-polypropylene-polystyrene (SEPS) type and/or polystyrene-b-poly(ethylene/propylene)-b polystyrene (SEEPS) type with high and ultrahigh molecular weights are used.

It is expedient to use hydrogenated polystyrene-polyethylene-polybutylene-polystyrene copolymers (SEBS, e.g., G1651, MD 6933, Kraton). Within the scope of the invention, hydrogenated polystyrene-b-poly(ethylene/propylene)-b-polystyrene copolymers (SEEPS, Septon 4055 and Septon 4077, Kuraray) are preferred.

To obtain a hydrophobic matrix according to the invention, at least one three-block elastomer of the SEBS or SEPS type, especially SEEPS with a very high molecular weight (at least 200,000 dalton, preferably at least 400,000 dalton) and with a Brookfield viscosity of at least 5000 mPas (for a 10% solution in toluene a 30° C.) is selected.

Such polymer compositions allow good inclusion of the fibers of the fabric as the backing, which thus remain completely isolated from the wound, so that no direct contact between fiber and regenerated tissue is risked at any time, which could result in a fiber inclusion in the wound, resulting in painful destruction of the tissue when the dressing is pulled away.

By using a mixture of the high-molecular and ultrahigh-molecular thermoplastic elastomers (TPE), a very soft compress is obtained which conforms well to the surface that is to be protected, while on the other hand, because of the strong cohesion and elasticity of the matrix even after radiation sterilization, is at no time so harmful, when applied to the wound according to the invention, that the fibers are exposed and come in direct contact with the wound. The amount of the ultrahigh-molecular polymer with a molecular weight of more than 300,000 dalton in the total polymer content is less than 50 wt %, in particular less than 25 wt % to maintain adequate processability. The desired improvement in sterilization stability under radiation sterilization is achieved when the amount of ultrahigh molecular polymer with a molecular weight of more than 300,000 dalton in particular approximately 400,000 to 450,000 dalton in relation to the total polymer content is more than 5%, in particular more than 10%, especially preferably 20% or more.

Due to the high oily plasticizer content, which is preferably obtained by starting with a mixture of mineral oil and petroleum jelly, in combination with a very low polymer/elastomer content, the matrix also acts like a pure fatty substance, which thus ensures very good tissue tolerability and properties of nonadhesion to the surface of the compress.

Of the products/plasticizers that are readily suitable for plasticizing the elastomer, reference may be made in particular to fatty substances that are liquid or solid at room temperature, in particular paraffin oils, medicinal white oils, mineral oils, ointment paraffins, petroleum jelly, silicone oils or silicone fats and/or waxes as well as mixtures thereof. Plasticizers such as petroleum jelly, whose drop point is between 35° C. and 70° C., are preferred. Medicinal white oils, whose purity requirements conform to Ph. Eur., are also preferred.

The matrix may also contain antioxidants. Suitable antioxidants include the sulfur antioxidants, for example, the zinc dibutyl dithiocarbamate marketed by the company Akzo Nobel Chemicals under the brand name Perkacit ZDBC and/or the phenolic antioxidants, for example, the products marketed under the brand names Irganox® 1010, Irganox® 565, Irganox® 1035 by the company BASF may also be mentioned as suitable antioxidants.

The compound in Irganox® 1010 is preferred within the scope of the present invention.

The wound contact layer of a wound dressing according to the invention according to the invention may also comprise an additive selected from the group consisting of another stabilizer, extrusion aids, fillers, pigments, dyes, crosslinking agents, odor suppressants, tackifiers, tolerability mediators, and combinations therefore.

The hydrocolloids, which are known in general (CMC, alginates, gelatin, xanthan, pectins) but also silicates such as bentonites, aerosils, or superabsorbers may be used as the hydrophilic organic and/or inorganic microparticles that bind water and undergo gelation in the process. Microparticles with a diameter of 50 to 300 μm (assuming a spherical shape), in particular with a diameter of 50 to 200 μm, are preferred.

The hydrocolloid dispersed in the elastomer matrix in a relatively small amount makes it possible to retain a slightly hydrophilic character, which is sufficient to maintain a moist wound environment that promotes wound healing, but is not sufficient to enable the gel to absorb a great deal of water. In fact, this absorption capacity is not desirable because it leads to swelling of the gel, which would cause a gradual clogging of the openings left in the structure of the compress. The compress would thus become occlusive which would thus suppress the option of eliminating the exudates while also increasing the risk of maceration and would clog the passages formed in the contact layer and cause maceration of the wound.

According to the present invention, a polymer composition comprising a nonabsorbent elastomer matrix/wound contact layer is made available.

With respect to the elastomer polymer matrix, the term "nonabsorbent" means that the hydrophobic matrix absorbs less than 35%, preferably less than 25% of the saline solution (aqueous 0.8% NaCl solution) in 24 hours, based on the dry weight of the matrix.

In elastomeric thermoplastic compositions, cohesion refers to the forces which hold the mass together. These cohesive forces are responsible for the toughness (viscosity) and flow behavior (rheology) of the elastomer matrix in processing and are also responsible for the strength of the matrix under stress. The cohesive forces in such systems are described by characteristic values such as the elastic modulus, tensile elongation, tensile strength and breaking strength/tensile force, or Shore hardness.

Tensile Strength and Tear Strength Testing

The tear strength is the quotient of the force $F_R$ (tearing force) measured at the moment of tearing and the initial cross section $A_0$ of the test sample, which is measured at the thinnest location.

The tensile strength is the quotient of the measured maximum force and the initial cross section of the sample body, which is measured at the thinnest location. In elastomers, the tearing force is usually also the maximum force.

Using a Zwick tensile testing machine, the tear strength and elongation at tear of the elastomer matrix were measured using sterile and nonsterile test bodies at an initial cross section $A_0$ of 100 mm². In determining the elongation at break, the length of a test body with an original length of 8 mm is determined on reaching the tearing force.

TABLE 1

Tear strength and elongation at tear of sterile and unsterile samples

| Type of sterilization | unsterile | | | radiation sterilization (gamma) | | |
|---|---|---|---|---|---|---|
| Dose | | | | 25-30 kGy | | |
| | Feature | | | | | |
| Sample | $F_R$ max [N] | Tear strength [cN/mm²] | Elongation at tear [mm] | $F_R$ max [N] | Tear strength [cN/mm²] | Elongation at tear [mm] |
| Example 1 | 2.97 | 2.97 | 614 | 1.69 | 1.69 | 544 |
| Example 1 | 2.80 | 2.80 | 579 | 1.48 | 1.48 | 395 |
| Example 1 | 2.80 | 2.80 | 581 | 1.55 | 1.55 | 490 |
| Average | 2.86 | 2.86 | 591 | 1.57 | 1.57 | 476 |
| Example 2 | 5.14 | 5.14 | 669 | 2.72 | 2.72 | 486 |
| Example 2 | 4.69 | 4.69 | 686 | 3.09 | 3.09 | 516 |
| Example 2 | 4.11 | 4.11 | 621 | 3.10 | 3.10 | 563 |
| Average | 4.65 | 4.65 | 659 | 2.97 | 2.97 | 522 |

Replacing small amounts (e.g., 0.6%) of the elastomer with a high molecular weight (as in example 1) with an ultrahigh molecular elastomer (as in example 2) completely compensates for the decline in tear strength and cohesion and increases stability of the polymer elastomer matrix with respect to radiation sterilization (sample of example 1, unsterile 2.86 cN/mm$^2$; sample of example 2, sterile 2.97 cN/mm$^2$). The negative effect of radiation sterilization on the elongation at tear is partially compensated.

Absorption of Saline Solution (NaCl 0.8%) in Wound Dressings After a Contact Time of 2 Hours, 4 Hours and 24 Hours A 10 cm$^2$ sample is weighed using an analytical balance (w1). A crystallizing dish is filled with saline solution so that the sample is completely covered with the test solution and there are only a few small air bubbles on it. At certain points in time, the sample is removed from the solution and patted carefully using a soft paper towel until all the water drops have been removed. The dry sample is then weighed using the analytical balance (w2).

Calculation of Absorption in % Based on the Polymer Matrix Weight (Pg) According to the Following Formula:

The weight of the backing (43 g/m$^2$) must be subtracted from the weight of the sample for this calculation.

$$\text{Absorption } (Pg)=[(w2-w1)/(w1-0.043)]\times 100$$

TABLE 2

Absorption of the saline solution after 2, 4, and 24 hours

| Averages | Absorption (Pg) in % after | | |
|---|---|---|---|
| | 2 h | 4 h | 24 h |
| Example 1 | 0.2 | 0.7 | 5.5 |
| Example 2 | 0.9 | 2.7 | 9.7 |

The absorption data from Table 2 demonstrates clearly that in an especially preferred embodiment of the invention, the elastomer wound contact layer does not absorb any mentionable amount of saline solution and therefore is not absorbent. The small quantities of water absorbed are utilized to form a boundary layer which contains fat and hydrocolloid gel and does not stick to the wound.

Wound dressings according to the invention can be obtained as follows:

EXAMPLE 1

| | Amount (g) | Parts by weight (%) |
|---|---|---|
| Paraffin oil | 1110 | 72.2 |
| Copolymer | 40 | 2.6 |
| Antioxidant | 1.5 | 0.1 |
| Petroleum jelly | 154 | 10.0 |
| CMC | 231 | 15.0 |

The composition is prepared in a laboratory dissolver. 1110 g of the paraffin oil is placed in the dissolver and mixed with 40 g of an elastomer copolymer SEEPS (Septon 4055, Kuraray) and 1.5 g of an antioxidant (Irganox 1010) and stirred at approximately 135° C. until obtaining a clear homogeneous elastomer composition. After incorporating 154 g petroleum jelly (Vara AB, Sasol) 231 g of the sodium carboxymethyl cellulose (CMC, Blanose 7H4XF, Aqualon) is added. The resulting elastomer composition is stirred for 30 minutes more until obtaining a homogeneous composition.

The composition may also be prepared in a kneader or similar installations/equipment known in general for processing hot melt compositions.

The composition can be applied to the fabric (mesh tulle) in an immersion bath at approximately 140-145° C., so that the textile structure is completely sheathed but the interspaces/pores remain largely open to ensure that the exudate can flow through.

EXAMPLE 2

Like example 1, except that a polymer mixture of 2% Septon 4055 and 0.6% Septon 4077 was used.

EXAMPLE 3

Like example 1, except that 15% of a nonionic cellulose derivative (HPMC, Bonucel D15000) was used.

Within the scope of the invention, it may be of particular importance for the wound dressings to absorb only in the range of 5% to 30% of the dry weight. This limits gelation and swelling (due to hydrocolloid solutions), so that the transport of exudate through the openings in the dressing and into the secondary dressing is not hindered.

Within the scope of the invention, the aspect wherein the backing has an open mesh so that an exudate flow can be ensured even after the fibers forming the backing have been coated/sheathed with the elastomer composition.

The invention is not limited to the exemplary embodiments described above. Instead, another idea involves the use of backing materials in the form of open mesh knits and woven fabrics and/or polyurethane foams, such as Vivo MCF 03 (AMS). The wound dressing according to the invention may also contain an additional active ingredient that is based on metals such as silver, copper, selenium, and/or based on metal compounds, in particular metal salts ($Ag_2O$, AgCl, ZnO, MgO), and is dissolved/dispersed/distributed in the elastomer matrix.

In an especially preferred embodiment of the invention the active ingredient comprises an oligomeric/polymeric biguanide, in particular polyhexamethylene biguanide (PHMB) (e.g., Cosmocil PQ, Arch) and/or an oligomeric/polymeric guanide and/or similar broad-spectrum antiseptics such as octenidine.

From the foregoing it will be seen that this invention is one well adapted to attain all ends and objectives hereinabove set forth, together with the other advantages which are obvious and which are inherent to the invention. Since many possible embodiments may be made of the invention without departing from the scope thereof, it is to be understood that all matters herein set forth are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A wound dressing comprising:
   a) a backing; and
   b) a non-absorbent elastomeric wound contact layer, said wound contact layer comprising an elastomeric matrix plasticized by an apolar oil, petroleum jelly or mixture thereof;

said elastomeric matrix formed from a mixture of:
at least one high molecular weight synthetic triblock elastomer with an average molecular weight of less than 300,000 daltons and
at least one ultrahigh molecular weight synthetic triblock elastomer with an average molecular weight of more than 300,000 daltons,
said synthetic triblock elastomers selected from the group consisting of polystyrene-polyethylene-polybutylene-polystyrene (SEBS), polystyrene-b-poly(ethylene/propylene)-b-polystyrene (SEEPS), polystyrene-polyethylene-polypropylene-polystyrene (SEPS) and mixtures thereof;
the total polymer content of the elastomeric matrix is less than 3.2% by weight;
the ultrahigh molecular weight synthetic triblock elastomer comprises approximately 10% to approximately 50% of the total polymer content; and
said elastomeric matrix having a molecular weight of 150,000 to 600,000.

2. The wound dressing according to claim 1, wherein at least one of the high molecular weight synthetic tri-block elastomer or ultrahigh molecular weight synthetic tri-block elastomer has a Brookfield viscosity of 5000 mPas or more for a 10% solution in toluene at 30° C.

3. The wound dressing according to claim 1, wherein the elastomeric matrix comprises an ionic or non-ionic hydrocolloid that is dispersed homogeneously in the matrix.

4. The wound dressing according to claim 1, wherein the backing comprises a material selected from a group consisting of open mesh knit, a woven fabric, a non-woven fabric, polyurethane foam, and mixtures thereof.

5. The wound dressing according to claim 1 wherein the elastomeric matrix has an active ingredient in a therapeutically effective amount.

6. The wound dressing according to claim 5, wherein the active ingredient is dissolved, dispersed or distributed homogeneously in the elastomeric matrix.

7. The wound dressing according to claim 5, wherein the elastomeric matrix does not contain active ingredient in all areas.

8. The wound dressing according to claim 5, wherein the active ingredient comprises metals, metal compounds, or mixtures thereof.

9. The wound dressing according to claim 8, wherein the metals or metal compounds comprise metal salts.

10. The wound dressing according to claim 5, wherein the active ingredient is selected from the group consisting of an oligomeric/polymeric biguanide, an oligomeric/polymeric guanide, a broad spectrum antiseptic and mixtures thereof.

11. The wound dressing according to claim 10, wherein the active ingredient is polyhexamethylene biguanide (PHMB).

12. The wound dressing according to claim 10, wherein the active ingredient is octenidine.

13. The wound dressing according to claim 1, wherein the elastomeric matrix contains a tackifier in order to increase the adhesive strength.

14. The wound dressing according to claim 1, wherein the wound dressing exhibits improved cohesion and elasticity upon radiation sterilization compared to a wound dressing that does not include an ultrahigh molecular weight synthetic triblock elastomer.

* * * * *